US007910367B2

(12) United States Patent
Besne

(10) Patent No.: US 7,910,367 B2
(45) Date of Patent: Mar. 22, 2011

(54) CELL CULTURE MODEL AND APPLICATIONS THEREOF

(75) Inventor: Isabelle Besne, Paris (FR)

(73) Assignee: L'Oreal, Paris (FR)

( * ) Notice: Subject to any disclaimer, the term of this patent is extended or adjusted under 35 U.S.C. 154(b) by 891 days.

(21) Appl. No.: 11/647,436

(22) Filed: Dec. 29, 2006

(65) Prior Publication Data
US 2007/0264682 A1 Nov. 15, 2007

Related U.S. Application Data

(60) Provisional application No. 60/759,974, filed on Jan. 19, 2006.

(30) Foreign Application Priority Data

Jan. 5, 2006 (FR) ...................................... 06 50047

(51) Int. Cl.
*C12N 5/07* (2010.01)
(52) U.S. Cl. ......................... 435/347; 435/297.1; 435/29
(58) Field of Classification Search .......................... None
See application file for complete search history.

(56) References Cited

U.S. PATENT DOCUMENTS

| 5,861,153 A * | 1/1999 | Schmidt et al. ............... 424/93.7 |
| 6,541,023 B1 | 4/2003 | Andre et al. |

FOREIGN PATENT DOCUMENTS

| FR | 2 809 412 A | 11/2001 |
| GB | 2 394 477 A | 4/2004 |
| WO | WO 03/005023 A2 | 1/2003 |
| WO | WO 2005/071065 A1 | 8/2005 |

OTHER PUBLICATIONS

Hilgenberg L. et al. Neural influence on protein kinase C isoform expression in skeletal muscle, The Journal of Neurosciences, Aug. 15, 1996, vol. 16, No. 16, pp. 4994-5003.*
Huang I.-T. et al. Influence of cutaneous nerves on keratinocyte proliferation and epidermal thickness in mice, Neuroscience, 1999, vol. 94, No. 3, pp. 965-973.*
G. Cardinali et al., "Keratinocyte Growth Factor Promotes Melanosome Transfer to Keratinocytes," Journal of Investigative Dermatology, vol. 125, No. 6, (2005) pp. 1190-1199.
M. Dobbie et al., "Do Neuronal Cells Influence the Formation of the Blood-Brain Barrier? Use of a Novel Tri-Culture System," European Journal of Neuroscience, vol. 12, No. Supplement 11, (2000) pp. 355.
M. Toyoda et al., "Calcitonin Gene-Related Peptide Upregulates Melanogenesis and Enhances Melanocyte Dendricity via Induction of Keratinocyte-Derived Melanotrophic Factors," Journal of Investigative Dermatology Symposium Proceedings, vol. 4, No. 2, (1999) pp. 116-125.
M. Regnier et al., "Keratinocyte-Melanocyte Co-Cultures and Pigmented Reconstructed Human Epidermis: Models to Study Modulation of Melanogenesis," Cellular and Molecular Biology, vol. 45, No. 7, (1999) pp. 969-980.

* cited by examiner

*Primary Examiner* — Jon P Weber
*Assistant Examiner* — Satyendra K Singh
(74) *Attorney, Agent, or Firm* — Oliff & Berridge, PLC

(57) ABSTRACT

Described is a multicellular model including at least, as cell type:
 keratinocytes,
 melanocytes, and
 nerve cells,
in which the keratinocytes and the melanocytes form a first cell layer, and the nerve cells form a second cell layer devoid of physical contact with the first cell layer, with the first and second cell layers being arranged so as to be compatible with a manifestation of at least one cellular chemical exchange.

15 Claims, 3 Drawing Sheets

CELL CULTURE MODEL AND APPLICATIONS THEREOF

This non-provisional application claims the benefit of French Application No. 06 50047 filed on Jan. 5, 2006 and U.S. Provisional Application No. 60/759,974 filed on Jan. 19, 2006.

BACKGROUND

The present invention relates to a multicellular model comprising keratinocytes, melanocytes and nerve cells, and also to the use of this model for the purposes of screening for active agents, in particular with regard to melanogenesis.

Numerous cell models aimed at simulating the various properties and characteristics of the skin had been developed in order to make it possible to carry out studies necessary for a better understanding of the role of the various elements constituting the skin, both in mechanical terms and in physiological terms.

In general, these models comprise human keratinocytes deposited onto a support, for example a dermis equivalent, and cultured under conditions suitable for the formation of an epidermal equivalent.

However, the skin is a complex structure comprising various cell types, where appropriate, organized in tissue structures, within which and between which cellular communications that regulate skin homeostasis can be established.

By way of example, skin comprises, in particular, keratinocytes, melanocytes and nerve cells, but also fibroblasts, Langerhans cells, endothelial cells constituting the blood vessels that irrigate the dermis and the hypodermis, smooth muscle cells, etc.

The keratinocytes are mainly responsible for the production of keratin, one of the essential constituents of the horny layer. They are continually undergoing a morphological evolution that is a reflection of their keratinization underlying the protective (mechanical, chemical) barrier role of the epidermis.

The melanocytes are located in the basal layer of the epidermis, they are the site of melanogenesis and, due to their close contact with the keratinocytes, they transfer to the latter the newly synthesized melanin in the form of melanosomes, thus giving the skin its coloration.

The type and the amount of melanin contained in the melanosomes determine the coloration of the skin. Melanin constitutes, in particular, an effective protective screen against solar radiation, in particular ultraviolet radiation.

Melanogenesis is a complex biological phenomenon initiated by hydroxylation of the L-tyrosine amino acid resulting from the formation of L-dihydroxyphenylalanine (L-DOPA), which is in turn converted to DOPA-chrome by the action of a specific melanocyte-associated enzyme, tyrosinase. Consecutive reduction and oxidation reactions result in the conversion of the DOPA-chrome to melanin. The production of tyrosinase and its activity determine in part the amount of melanin produced. The amount and the type of melanin transferred to the keratinocytes determine, for their part, the degree of visual pigmentation of human skin.

Now, melanin can be synthesized excessively, or even anarchically, in response to an exogenous stress such as pollution and UV rays, and/or an endogenous stress, for example due to ageing of the keratinocytes, the endothelial cells, the fibroblasts and the Langerhans cells.

Thus, many skin disorders can result from a disruption of melanogenesis and result, for example, in an overload of melanin or in an abnormal distribution of melanin in the skin, called hypermelanosis. In hypermelanoses, melanoderma, an anomaly associated with the epidermis, and ceruloderma, a dermal anomaly, can be distinguished.

Recently, it has been noted that emotional stress, for example of neurogenic origin or involving nerve cells, can induce a release of hormones and of neurohormones capable of affecting the homeostasis of melanogenesis.

Now, to date, none of the available cell models makes it possible to reproduce and study the impact of nerve activity, satisfactorily, on the physiological functions of the skin, in particular on melanogenesis.

The present invention is aimed at precisely satisfying this need.

SUMMARY

Thus, a subject of the present invention, according to one of its aspects, is a multicellular model comprising at least, as cell type:
 keratinocytes,
 melanocytes, and
 nerve cells,
in which the keratinocytes and the melanocytes form a first cell layer, said nerve cells form a second cell layer devoid of physical contact with the first cell layer, said first and second cell layers being arranged so as to be compatible with a manifestation of at least one cellular chemical exchange.

BRIEF DESCRIPTION OF THE DRAWINGS

FIG. 2 represents the growth of nerve endings of nerve cells of a nerve cell-keratinocyte-melanocyte multicellular model, through the porous insert on which they are cultured.

DETAILED DESCRIPTION

Figure 1:
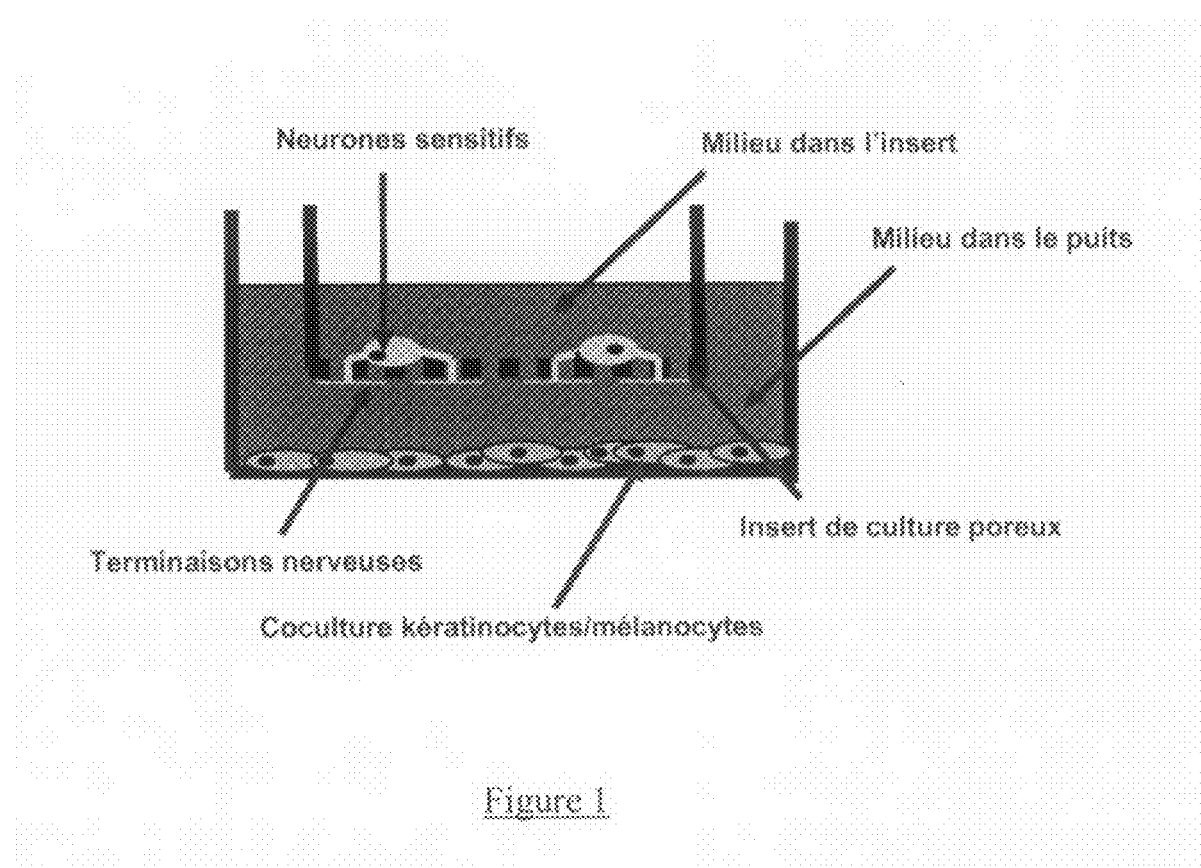
FIG. 1 is a schematic representation of a multicellular model of keratinocyte/melanocyte/nerve cell triculture.

The cellular model according to the invention may be easy to use, robust, and may make it possible to study the physiological mechanisms that regulate skin homeostasis, such as melanogenesis.

The cellular model according to the invention may also be simple to use, and may not require direct contact between the nerve cells and the other cells, as for example with the cocultures of melanocytes and of keratinocytes.

Thus, the inventors have observed that the application of noradrenalin in a multicellular model according to the invention leads to an increase in the release of Calcitonin-Gene-Related Peptide (CGRP) from nerve cell endings, and also an increase in melanin synthesis by melanocytes. On the other hand, the administration of a CGRP receptor antagonist, $CGRP_{8-37}$, is reflected more particularly by a considerable decrease in melanin synthesis, thus attesting to the involvement of CGRP in a cellular chemical exchange between the nerve cells and the melanocytes.

A subject of the present invention, according to another of its aspects, is the use of a multicellular model in accordance with the invention for screening for agents capable of modulating a manifestation of a chemical exchange that may take place between nerve cells, keratinocytes and/or melanocytes.

A subject of the present invention, according to another of its aspects, is a method for screening for agents capable of modulating a manifestation of a chemical exchange that may take place between nerve cells, keratinocytes and/or melanocytes comprising a step of using a multicellular model in accordance with the invention.

A subject of the present invention, according to yet another of its aspects, is a method for screening for agents capable of modulating melanogenesis, comprising at least the steps consisting in:
a) providing a multicellular model in accordance with the invention under conditions suitable to the manifestation of melanogenesis,
b) placing said model in the presence of at least one agent to be screened, under conditions suitable to an interaction with said model, and
c) determining the amount of melanin produced by said model, at the end of step b).

Thus, the model according to the invention may make it possible to determine new biological targets that may be involved in skin disorders resulting from an impairment of melanogenesis.

Similarly, a multicellular model according to the invention may also prove to be useful for screening for agents capable of modulating melanogenesis and of identifying new therapeutic and/or cosmetic agents that are effective for depigmentation or propigmentation.

For the purpose of the invention, "multicellular" is intended to mean at least three distinct cell types.

For the purpose of the present invention, the expression "cell layer" is intended to denote a set of cells, which may or may not be at confluence, as a monolayer or as a multilayer, arranged in the same plane.

For the purpose of the invention, the expression "cellular chemical exchange" is intended to denote all the signals shown by molecules, released from a cell, and liable to affect, remotely, the activity of another cell, which may or may not belong to the same cell type. Such a molecule may, for example, and in a nonlimiting manner, be a peptide, a protein, a lipid, a sugar, a steroid hormone or a catecholamine. It may be released in the form of a secretion, for instance the release of CGRP molecules.

For the purpose of the present invention, the expression "devoid of physical contact" is aimed at denoting an arrangement in which the first and the second cell layers, which may or may not be placed in a single chamber, are connected to one another by means of the culture medium in which they are incubated, without cells of one layer being able to come into direct contact with cells of another layer, for example by contact between the cell bodies or by means of cell extensions, such as axons or dendrites. The expression "devoid of physical contact" may mean in particular, that nerve cells do not form synaptic contact with the other cell types present in a model of the invention.

Thus, in a multicellular model according to the invention, the nerve cells of the second cell layer do not innervate the cells of the first cell layer.

For the purpose of the invention, the term "modulate" is intended to denote an increase or a decrease in a biological activity of a given cell, for example melanogenesis.

Multicellular Model

The multicellular model according to the invention comprises a first cell layer comprising keratinocytes and melanocytes, and a second cell layer comprising nerve cells.

The first and second cell layers are devoid of physical contact with one another and are arranged so as to be compatible with the manifestation of at least one cellular chemical exchange.

By way of example of a chamber suitable for implementing the invention, mention may be made of wells of culture plates such as 6-, 12-, 24-, 48-well or 96-well cell culture plates, normally used in cell culture.

According to one embodiment, the first and/or the second cell layer(s) can be placed on and/or in a porous or semi-permeable support.

The term "porous support" is intended to mean an insert, the base of which comprises pores.

The size of the pores will be adjusted by those skilled in the art so as to allow, possibly, the development of cell extensions without direct contacts being established between the first and the second cell layers. For example, the pore size may range from 0.001 to 10 µm, and may be greater than or equal to 0.5 µm. By way of nonlimiting example, the base of the porous insert suitable for the invention may thus comprise a porous matrix of collagen, optionally comprising glycosaminoglycans and/or fibroblasts, a gel or a membrane of hyaluronic acid and/or of collagen and/or of fibronectin and/or of fibrin, a semi-permeable membrane of nitrocellulose, of Nylon®, of Teflon®, of polycarbonate, of polyethylene, of polypropylene or of polyethylene terephthalate (PET), a semi-permeable Anopore® inorganic membrane, a cellulose acetate membrane, a Biopore-CM® semi-permeable membrane, a semi-permeable polyester membrane and a polyglycolic acid membrane.

For example, it is possible to form two planes of cell layers by culturing a first set of cells in a culture insert, and then by placing this or these insert(s) in culture plates, the bottom of which comprises a second set of cells forming a second cell layer.

According to one embodiment, a porous support suitable for the implementation of the present invention may be an insert arranged so as to be placed in a cell culture plate well without being in direct contact with the bottom of said well.

Thus, such a support may comprise lugs, hooks or any other means for keeping it at an appropriate distance from the bottom of a cell culture plate well, and in particular from the cell layer that is optionally placed thereon.

By way of example of an insert suitable for the implementation of the invention, mention may be made, non-exhaustively, of the transparent or opaque PET (polyethylene terephthalate) membrane insert of the Falcon®, Nunc® or Costar® trademark. Inserts particularly suitable for the implementation of the invention are also the inserts sold under the reference Thincert, the porosity of which is 1 µm (ref: 662610), by the company Greiner Bio-One.

The first and second cell layers can be arranged so as to divide a single chamber into at least two compartments.

According to one embodiment, said first and second cell layers can be arranged along parallel planes.

According to one embodiment, the first and second cell layers can be arranged along horizontal parallel planes, and in particular in which the second layer represents an upper plane.

According to one embodiment, the upper plane can be formed by a bottom of an insert in which the second cell layer is placed.

The bottom of the insert may have a porosity suitable for the development of nerve endings outside said bottom, in order to promote the expected chemical exchange without, however, direct contact, in particular by innervation, being established between the cell layers.

Such a suitable insert can be selected from the group consisting of the porous supports defined above.

According to this embodiment, the first cell layer is, for its part, placed at the bottom of the chamber, optionally on a support more particularly selected from the group consisting of a collagen matrix, optionally comprising fibroblasts and/or glycosaminoglycans, a de-epidermalized dermis, a dermis equivalent, a hyaluronic acid and/or collagen and/or fibronectin and/or fibrin membrane, and an inert support.

According to one embodiment, the multicellular model in accordance with the invention can also comprise at least one additional cell type, for example selected from the group consisting of endothelial cells, immune system cells such as Langerhans cells, T lymphocytes, dendritic cells or macrophages, or else adipocytes. Said additional cell type(s) can be cocultured with the first and/or the second cell layer.

An example of implementation of a multicellular model in accordance with the invention can be obtained as follows.

A coculture of keratinocytes and of melanocytes can be carried out according to standard cell culture conditions, directly on the bottom of a culture plate.

This coculture is generally initiated by seeding the wells with either melanocytes or keratinocytes, in particular as defined in the examples hereinafter. After a period of time suitable for the adhesion of the seeded melanocytes or keratinocytes, and generally ranging from a few hours to a few days, in particular between 1 hour and 72 hours, the second cell type, keratinocytes or melanocytes, as appropriate, can be seeded into the wells containing the first cell type previously introduced.

The cell densities to be used for the seeding of the culture plates with the keratinocytes and the melanocytes can be adjusted according to various factors, such as the cell type, the cell size, the proliferation rate of the cells, or the surface area of the wells. Such an adjustment amounts to routine practice for those skilled in the art.

Nerve cells can be cultured on a porous support, such as, for example, Thincert inserts mentioned above.

By way of example of nerve cells suitable for the implementation of the invention, mention may be made of animal or human sensory nerve cells present in the skin and capable of releasing neuromediators, or nerve cells capable of releasing any factor capable of modulating melanogenesis. They may also be human neuronal cell lines (original or metastatic) that exhibit the characteristics of nerve cells with release of neurohormones or neurotransmitters.

After a suitable culture period, generally 2 to 6 days, the nerve cells, placed in and/or on an insert or in and/or on a porous support, can be introduced into a cell culture plate well comprising a coculture of keratinocytes and melanocytes.

All the cells of a multicellular model in accordance with the invention can be cultured in a medium suitable for the maintenance and/or the growth and/or the proliferation of each of the cell types of the multicellular model in accordance with the invention.

Numerous culture media that may be suitable for the implementation of the invention can be obtained commercially. By way of nonexhaustive examples of culture media suitable for the invention, mention may be made of Dulbecco's Modified Eagle's Medium (DMEM), Minimal Essential Medium (MEM), M199, RPMI 1640 or Iscove's Modified Dulbecco's Medium (EDMEM), Ham's F-12, Ham's F-10, NCTC 109 and NCTC 135.

These media can be supplemented with any additive conventionally used in cell culture, such as, for example in a nonlimiting manner, phospholipid precursors, non-essential amino acids, nucleic acids, vitamins, antibiotics, enzymatic cofactors, mineral salts, insulin, transferrin, triiodothyronine, ethanolamine, o-phosphorylethanolamine or growth factors such as nerve growth factor or neurotrophin-3.

The concentrations of the various additives normally used for supplementing the cell culture media can be determined and adjusted by those skilled in the art, in particular according to the cell type to be cultured.

Other media are described in Ham and McKeehan, "*Methods in Enzymology*", 58:44-93, 1979, or else in Bottenstein et al., "*Methods in Enzymology*", 58:94-109, 1979.

Moreover, it is also possible to use mixtures of various media, in particular of the abovementioned media, for instance a mixture of DMEM/HAM F12.

By way of nonlimiting example of a culture medium suitable for the implementation of the invention, mention may be made of a coculture medium comprising a mixture of DMEM-HAM F12 media sold by the company Invitrogen under the reference 21331-020, and of M154 media sold by the company Tebu under the reference M154 CF/PRF.

According to an embodiment, a multicellular model of the invention may be implemented with a culture medium as defined in the following examples illustrating the invention.

This medium may also be supplemented with one or more of the additives conventionally used in cell culture, such as, for example, L-glutamine, antibiotics such as penicillin or streptomycin, growth factors such as nerve growth factor (NGF), neurotrophin-3 (NT-3) or a human keratinocyte growth factor (human keratinocyte growth supplement, HKGS), or mineral salts such as calcium chloride ($CaCl_2$).

In general, a multicellular model in accordance with the present invention can be maintained under culture conditions for maintaining cell survival and/or growth and/or cell proliferation for a period ranging from approximately 5 to 15 days, under standard culture conditions.

Under these conditions, the melanocytes can perform a melanogenesis representative of a physiological basal state.

Use of the Multicellular Model

It should be noted that a cellular model in accordance with the invention is not limited to solely the implementation of the study of the influence of nerve cells on melanogenesis. It falls within the practice of those skilled in the art to envisage numerous variants of the invention without departing from the scope of the latter.

Thus, it may also be envisaged, for example and in a nonlimiting manner, to use a model in accordance with the invention for studying the influence of the activity of nerve cells on keratinocytes, or the influence of the activity of melanocytes on the activity of nerve cells or of keratinocytes, etc.

By way of example of a cellular chemical exchange considered in a multicellular model in accordance with the invention, mention may also be made of all the extracellular signals that ensue from the application, on nerve cells, of a neurotransmitter of adrenergic type, such as noradrenalin (NA), or cholinergic type, such as acetylcholine, or of agonists that mimic the activity of these substances, such as, respectively, isoproterenol or nicotine or muscarine.

The cellular chemical exchange considered may have a modulatory effect with regard to a biological activity of at least one cell type.

By way of example of a biological activity that may be modulated by a cellular chemical exchange considered in a multicellular model according to the invention, mention may be made of melanogenesis or else neurotransmitter release.

According to one embodiment, a biological activity may be melanogenesis.

A modulation of melanogenesis may result from a cellular chemical exchange capable of being carried out directly between nerve cells and melanocytes, or possibly by comprising an intermediate stage at the level of the keratinocytes.

According to one embodiment, the chemical exchange that may be modulated by a screened agent may have a modulatory effect with regard to melanogenesis.

This implementation of this aspect of the invention may be carried out according to a method for screening for agents, comprising at least the steps consisting in:
a) providing a multicellular model in accordance with the invention,
b) placing said multicellular model in the presence of at least one agent to be screened, and
c) determining the amount of melanin produced by said model at the end of step b).

The multicellular model according to the invention provides conditions suitable to the manifestation of melanogenesis.

According to an embodiment, the amount of melanin produced at the end of step c) can be compared with an amount of melanin produced by a model in accordance with the invention in the absence of agent to be screened and/or in the presence of a reference molecule, the effect of which on melanogenesis is known, for example a melanogenesis inhibitor such as $CGRP_{8-37}$, or, for example, a melanogenesis activator such as noradrenalin.

The agent to be screened is placed in the presence of the cellular model in step b) and under conditions suitable to an interaction with said model, in particular by contact with at least one of the cell types in culture and/or at least one culture medium for said cells, in particular in an insert and/or in a well.

According to an embodiment, the agent to be screened may be capable of modulating melanogenesis by acting on the nerve cells and/or melanocytes and/or keratinocytes.

An agent to be screened may, for example, be a melanogenesis inhibitor that acts directly on the melanocytes, a melanogenesis inhibitor that acts on the nerve cells, a melanogenesis inhibitor that acts on the keratinocytes, a melanogenesis-stimulating agent that acts directly on the melanocytes, a melanogenesis-stimulating agent that acts on the keratinocytes, or a melanogenesis-stimulating agent that acts on the nerve cells, for example by stimulating the release of a molecule capable of activating, in return, melanogenesis in the melanocytes.

According to an embodiment, the melanogenesis can be stimulated by using, in step a), an agent that activates or inhibits a cell type.

Such an agent may stimulate the nerve cells and thus increase the release of chemical mediators.

The agent may be selected the group consisting of from adrenergic agonists such as noradrenalin or adrenalin.

In fact, it has been observed, in the context of the invention, that the stimulation of melanogenesis by noradrenalin takes place not only by direct stimulation, but may involve an intermediate factor released by the nerve endings.

Thus, it is, for example, possible to stimulate the activity of nerve cells by bringing the latter into contact with an agent that stimulates their activity, such as a noradrenergic agonist, for instance noradrenalin. This nerve cell activation may then result in a release of neurohormones, for instance CGRP, which can, in turn, act on the melanocytes by stimulating melanogenesis.

An agent to be screened can be brought into contact with a multicellular model in accordance with the invention before, after or simultaneously with the addition of an agent that activates or inhibits a cell type.

The placing of an agent that activates or inhibits a cell type, in the presence of an agent to be screened in step b) can be carried out for a period of time suitable for making it possible to determine a possible variation in the amount of melanin.

For example, the incubation time for noradrenalin in the absence or presence of an agent to be screened may be from approximately 5 to 12 days, and in particular approximately 10 days.

According to one embodiment, the amount of melanin produced by a model according to the invention, in the absence of agent to be screened and of agent that activates or inhibits a cell type, can be compared with an amount of melanin obtained in the presence of an activating or inhibiting agent, but in the absence of an agent to be screened, and with an amount of melanin obtained in the presence of these two types of agents.

These various amounts of melanin can be obtained in parallel in the same series of experiments.

The amount of melanin produced by the melanocytes can be determined, for example, by measuring the optical density, for example at 405 nm, after extraction of said melanin by any suitable techniques known to those skilled in the art.

For example, it is possible to extract the melanin by means of a solution of sodium hydroxide (NaOH at 0.5 N).

The optical density values measured can then be compared with an exogenous melanin range, for example ranging from approximately 0.3 to approximately 100 µg/ml of melanin.

A multicellular model in accordance with the invention can also be used for identifying at least one molecule that may be involved in a manifestation of a cellular chemical exchange that may take place between nerve cells, keratinocytes and/or melanocytes.

According to one embodiment, the chemical exchange considered may have a modulatory effect with regard to melanogenesis.

Thus, a multicellular model according to the invention can be used, for example, for the purposes of identifying molecules that may be released by nerve cells and that may act on melanocytes so as to modulate melanogenesis.

The identification of such molecules may be carried out by any suitable techniques known to those skilled in the art, for example using a sample of culture medium taken from a cellular model in accordance with the invention.

The means of identification that may be used may be, for example, an ELISA, a method of analytical separation by chromatography, for example a high performance liquid chromatography, optionally coupled to a mass spectrometer, an NMR or an infrared spectrometer.

Numerous modifications of the invention as disclosed above may be envisaged by those skilled in the art without departing from the scope thereof.

Such modifications are covered by the present application.

The invention is illustrated by the following examples, which should not be interpreted as limiting the scope of the present invention.

FIG. 1: Schematic representation of a multicellular model of keratinocyte/melanocyte/nerve cell triculture.

The insert is introduced into the culture well such that the keratinocytes, the melanocytes and the nerve cells are cultured in the same culture medium in order to allow intracellular chemical exchanges.

FIG. 2: Represents the growth of nerve endings of nerve cells of a nerve cell-keratinocyte-melanocyte multicellular model, through the porous insert on which they are cultured.

The photographs were taken by epifluorescence microscopy after labeling of the nerve cells with a tubulin antibody and visualization with an anti-immunoglobulin antibody labeled with Alexa Fluor 488. They were taken below the insert (on the keratinocyte-neurone site).

The arrows indicate the extensions that have crossed the support and are developing on the cultural side.

The white bar represents 5 μm.

Figure 2A:
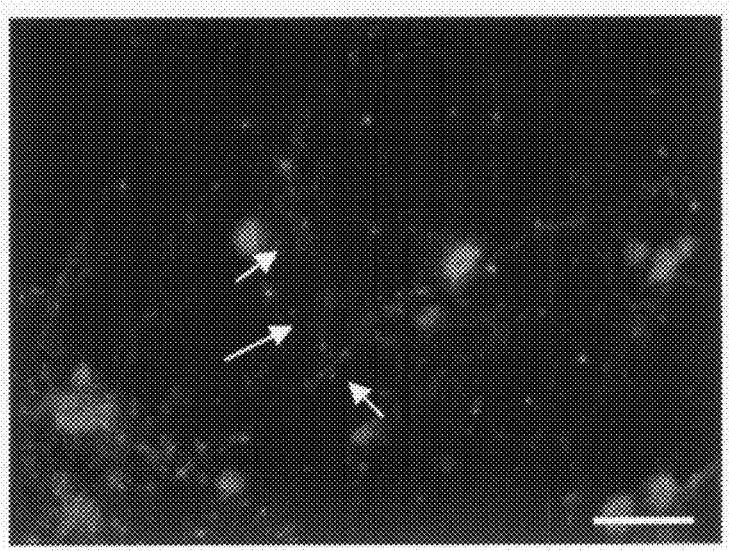
FIG. 2a represents nerve cells cultured in the absence of noradrenalin.
Figure 2B:
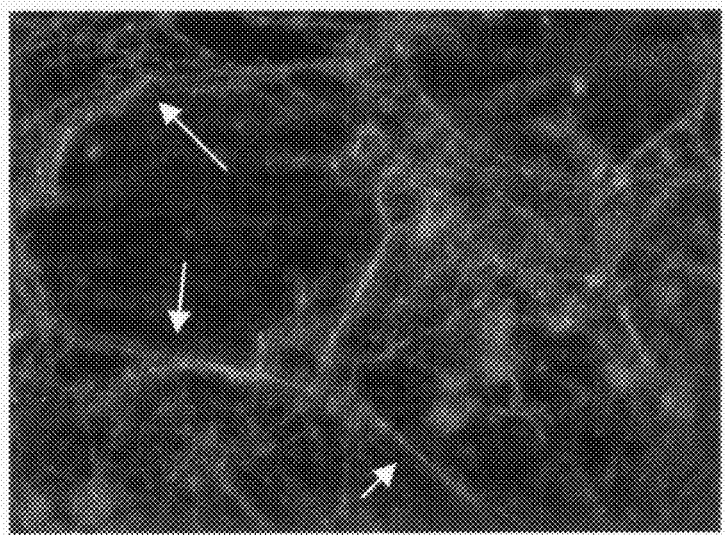
FIG. 2b represents nerve cells cultured in the presence of noradrenalin at $10^{-5}$ M.

FIG. 2a represents nerve cells cultured in the absence of noradrenalin, and FIG. 2b represents nerve cells cultured in the presence of noradrenalin at $10^{-5}$ M.

Figure 3:
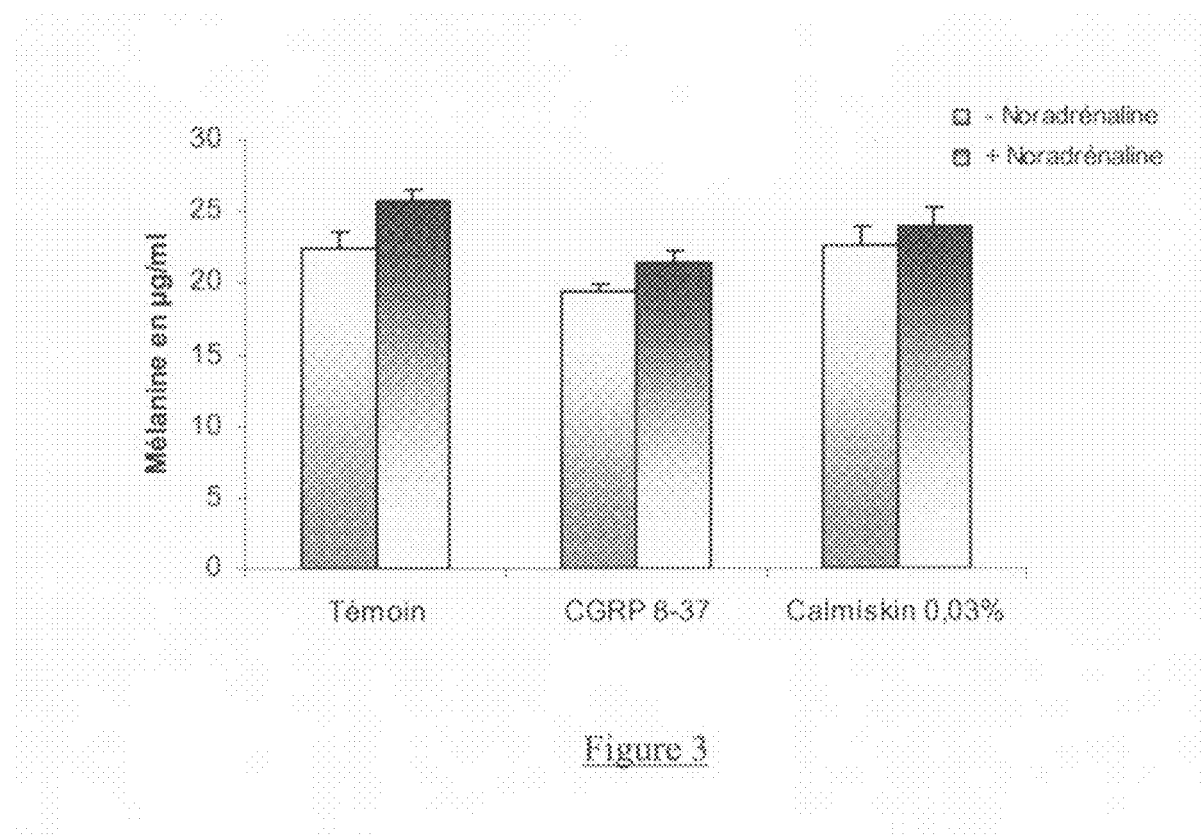
FIG. 3 represents the modulation of melanogenesis by the activity of nerve cells.

FIG. 3: Represents the modulation of melanogenesis by the activity of nerve cells. The nerve cells of a multicellular model according to the invention are stimulated, or not, with noradrenalin for 10 days and, where appropriate, in the presence of $CGRP_{8-37}$ or of Calmiskin® at 0.03%.

EXAMPLES

Example 1

Preparation of a Multicellular Model of Keratinocytes/Melanocytes/Nerve Cells

A first culture was prepared from sensory neurons (N) cultured in culture inserts for a 24-well plate (ThinCert™, Greiner bio-one ref. 662 610) in a DMEM-HAM F12 culture medium (Invitrogen 21331-020) supplemented with 2 mM L-glutamine (Invitrogen 25030024), 50 IU/ml penicillin-50 μg/ml streptomycin (Invitrogen 15070063), an N2 supplement (17502-048), a nerve growth factor (NGF, Invitrogen 13290.010) and neurotrophin 3 (NT-3, Tebu 450-03-b).

These inserts have a surface area of $0.33\ cm^2$ and a porosity of 1 μm. They also have the property of being transparent, which makes it possible to observe the cells.

20 000 neuronal cells were seeded per insert in defined medium for the culture of sensory neurons in an incubator at 37° C. and 5% $CO_2$, at saturated humidity.

The neurons were maintained in culture for 4 days in an incubator maintained at 37° C., in an atmosphere of 5% $CO_2$.

A second culture was prepared with keratinocytes (K) (normal human keratinocytes (NHEK) isolated from plastic surgery and used at the $3^{rd}$ passage) seeded at a rate of 100 000 cells/well, in a 24-well plate, in medium (medium 254 (Tebu 058M-254-500)) supplemented with HMGS-2 without PMA (Tebu 058S-016-5) and a mixture of 50 IU/ml penicillin and 50 μg/ml streptomycin.

After adhesion for 3 hours, melanocytes (M) (normal human epidermal melanocytes (NHEM-2) used at the $6^{th}$ passage) were seeded, at a rate of 50 000 cells/well, into the keratinocyte cultures.

The keratinocytes-melanocytes were maintained in culture for 1 day, in an incubator maintained at 37° C., in an atmosphere of 5% $CO_2$.

After 4 days of culture, the inserts containing the nerve cells were deposited into the wells containing the keratinocyte/melanocyte coculture (after one day of culture of the coculture), so as to obtain the nerve cell-keratinocyte-melanocyte (N/K/M) multicellular model, in the presence of N/K/M culture medium.

The N/K/M culture medium comprises a 50-50 mixture of DMEM-HAM F12 medium (Invitrogen 21331-020) supplemented as indicated above, 50 IU/ml penicillin, 50 μg/ml streptomycin (Invitrogen 15070063), and a supplement, and of medium M 154 (Tebu M 154 CF/PRF) supplemented with $CaCl_2$ (Tebu S-013-154) and a keratinocyte growth factor (Complement Human Keratinocytes Growth supplement HKGS Tebu S-001-5).

The multicellular model thus obtained was maintained in culture for at least 10 days.

The culture medium of the well and of the insert was renewed 50/50 each day.

A scheme illustrating the multicellular model thus obtained is represented in FIG. 1.

Example 2

Demonstration of the Growth of Nerve Endings Through a Porous Support

Using a multicellular model as obtained in Example 1, the cells were cultured in the absence or presence of $10^{-5}$ M noradrenalin, for 10 days.

The N/K/M culture medium was deposited into the culture wells and into the inserts.

The various media were renewed 50/50 every day.

The nerve cells were labelled with an anti-β-tubulin monoclonal antibody (Sigma T8660) and then visualized with goat anti-mouse immunoglobulin antibody-Alexa fluor 488 conjugate (Interchim A-11029).

After thorough washing in PBS, the preparations were observed by epifluorescence (Nikon Diaphot 300 microscope) and photographed.

The images are represented in FIG. 2.

The photographs were taken below the insert (on the keratinocyte-neuron site).

The arrows indicate the extensions that have crossed the support and are developing on the culture well side.

The white bar represents 5 μm.

FIG. 2a represents nerve cells cultured in the absence of noradrenalin, and FIG. 2b represents nerve cells cultured in the presence of noradrenalin at $10^{-5}$ M.

It is noted that, in the presence of the noradrenalin, the density of the cell extensions is increased.

Example 3

Effects of a Noradrenergic-Type Emotional Stress on Melanogenesis

Cells of a multicellular model as obtained in Example 1 were maintained for 10 days in the absence or presence of $10^{-5}$ M noradrenalin, non-supplemented or supplemented with 0.03% Calmiskin® or with $10^{-6}$ M $CGRP_{8-37}$, according to a protocol similar to that described in Example 2.

$CGRP_{8-37}$ is a reference CGRP receptor antagonist.

The Calmiskin® product is a solution of an extract of mint leaf (*Mentha piperita*) at 100% (v/v) in water and is distributed by the company Silab.

At the end of the incubation, the melanin was extracted from the keratinocyte/melanocyte cocultures with a solution of 0.5 N NaOH, and then quantitatively determined by measuring the optical density (405 nm) and compared with a standard range of exogenous melanin (0.39-100 μg/ml of melanin, Sigma M8631).

The experimental data were analyzed by means of the PRISM® software (graph pad software).

The intergroup comparisons were carried out by analysis of variance (ANOVA) using Dunnett's multiple comparison test.

The comparisons between two samples were carried out by analysis using the T test.

The results obtained are given in the table below. They represent the mean of 4 independent experiments. They are expressed in μg of melanin/ml.

|  | Without noradrenalin | +noradrenalin |
| --- | --- | --- |
| Control | 22.4 ± 1.12 | 25.77 ± 0.72# |
| $10^{-6}$M CGRP$_{8-37}$ | 19.33 ± 0.48 | 21.35 ± 0.91# |
| 0.03% Calmiskin ® | 22.57 ± 1.30 | 23.89 ± 1.32* |

The presence of $10^{-5}$M noradrenalin significantly stimulates (#; $p<0.01$) the amount of melanin synthesized in the cocultures (+15%).

The Calmiskin® product at the concentration of 0.03%, and also the CGRP receptor antagonist, CGRP$_{8-37}$, significantly decrease (*; $p<0.05$ and #; $p<0.01$) the amount of melanin (−7.3% and −17.2%, respectively) in the presence of noradrenalin.

Example 4

Measurement of CGRP Release

At the end of the experiment described in Example 3, the supernatants from the wells and from the inserts were collected separately and immediately frozen at −80° C. in order to analyze the CGRP content.

The CGRP content was measured in the culture supernatants by means of an ELISA assay (Rat CGRP enzyme Immuno Assay Kit, Spi Bio A05482) according to the protocol recommended by the supplier.

The results are expressed in μg of CGRP/ml of medium.

The analysis of the results was carried out as described above.

|  | Culture well | Insert |
| --- | --- | --- |
| −Noradrenalin | 159.31 ± 21.24 | 417.12 ± 37.33 |
| +$10^{-5}$M Noradrenalin | 170.48 ± 19.47 | 493.86 ± 11.57 |
| $10^{-5}$M Noradrenalin + 0.03% Calmiskin ® | 134.11 ± 14.66* | 474.19 ± 12.46 |

*p < 0.05

In the presence of noradrenalin, the amount of CGRP released in the insert of the control culture is very substantial. The Calmiskin® product slightly modulated the CGRP release.

The amount of CGRP assayed in the culture medium of the wells (in contact with the keratinocyte/melanocyte coculture) shows that the CGRP diffused or was released by the nerve endings that had crossed the porous insert. At this level, the Calmiskin® product significantly decreased the CGRP release (−21% of the control; $p<0.05$).

CONCLUSION

The addition of noradrenalin to a multicellular model according to the invention induces an increase in the amount of CGRP released into the culture medium by the nerve cells.

This amount is greater at the level of the nerve cells, but is also measurable in proximity to the keratinocyte/melanocyte coculture.

Noradrenalin thus appears to increase melanogenesis in a measurable manner (+15%) at the level of the keratinocyte/melanocyte coculture by means of CGRP release.

This stimulation was decreased by application of the Calmiskin® product at the concentration of 0.03%.

The invention claimed is:

1. A multicellular model comprising at least, as cell type:
   keratinocytes,
   melanocytes, and
   nerve cells,
   and a porous or semi-permeable insert having a pore size range from 0.001 to 10 μm,
   in which the keratinocytes and the melanocytes form a first cell layer, and the nerve cells form a second cell layer devoid of direct physical contact with the first cell layer, the first and second cell layers being arranged with the porous or semi-permeable insert between said layers so as to divide a single chamber into at least two compartments and be compatible with a manifestation of at least one cellular chemical exchange; wherein the first and/or the second cell layer(s) is (are) placed on and/or in the porous or semi-permeable insert.

2. The multicellular model according to claim 1, wherein the cellular chemical exchange has a modulatory effect with regard to a biological activity of at least one cell type.

3. The multicellular model according to claim 2, wherein the biological activity is melanogenesis.

4. The multicellular model according to claim 1, wherein the porous insert is selected from the group consisting of a collagen matrix, a gel or a membrane of hyaluronic acid and/or collagen, fibronectin and/or fibrin, a semi-permeable membrane of nitrocellulose, of Nylon®, of Teflon®, of polycarbonate, of polyethylene, of polypropylene or of polyethylene terephthalate (PET), a semi-permeable Anopore® inorganic membrane, a cellulose acetate membrane, a Biopore-CM® semi-permeable membrane, a semi-permeable polyester membrane, and a polyglycolic acid membrane.

5. The multicellular model according to claim 1, wherein the first and second cell layers are arranged along parallel planes.

6. The multicellular model according to claim 5, wherein the first and the second cell layer are arranged along horizontal parallel planes.

7. The multicellular model according to claim 6, wherein the second cell layer represents an upper plane.

8. The multicellular model according to claim 7, wherein the upper plane is formed by a bottom of the insert, in which the second cell layer is placed.

9. The multicellular model according to claim 1, wherein the first cell layer is placed on a support selected from the group consisting of a collagen matrix, a de-epidermalized dermis, a dermis equivalent, a membrane of hyaluronic acid, fibronectin, collagen, fibronectin and/or fibrin, and an inert support.

10. The multicellular model according to claim 1, comprising at least one additional cell type selected from the group consisting of endothelial cells, immune system cells and adipocytes.

11. A method for screening for agents capable of modulating melanogenesis, comprising at least the steps of:
   a) providing the multicellular model as defined in claim 1,
   b) placing the model in the presence of at least one agent to be screened, and
   c) determining the amount of melanin produced by the multicellular model, at the end of step b);
   wherein the amount of melanin at the end of step c) is compared with an amount of melanin produced by the model in the absence of the agent screened.

12. The method according to claim 11, wherein the melanogenesis is stimulated by using, in step a), an agent that activates or inhibits a cell type.

13. The method according to claim 12, wherein the agent stimulates the nerve cells.

14. The method according to claim 12, wherein the agent is chosen from adrenergic agonists.

15. The method according to claim 11, wherein the agent to be screened is capable of modulating melanogenesis by acting on the nerve cells and/or melanocytes and/or keratinocytes.

* * * * *